US 6,586,252 B2

(12) United States Patent
Kang et al.

(10) Patent No.: US 6,586,252 B2
(45) Date of Patent: Jul. 1, 2003

(54) NUCLEIC ACID MOLECULE ENCODING THE CATALYTIC SUBUNIT OF A PROTEIN PHOSPHATASE 2A THAT REGULATES FLOWERING TIME IN PLANTS

(75) Inventors: Jeong-Gu Kang, Kwangju (KR); Pill-Soon Song, Kwangju (KR); Chung-Mo Park, Kwangju (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 0 days.

(21) Appl. No.: 09/916,338

(22) Filed: Jul. 30, 2001

(65) Prior Publication Data

US 2003/0028924 A1 Feb. 6, 2003

(51) Int. Cl.[7] ...................... C12N 15/29; C12N 15/54; C12N 15/82; C12N 5/04; C12N 5/10
(52) U.S. Cl. ..................... 435/468; 435/320.1; 435/419; 435/194; 536/23.6; 536/24.5
(58) Field of Search ................................. 800/290, 298, 800/286; 536/23.1, 23.6, 24.5; 435/419, 468, 252.33, 194, 320.1

(56) References Cited

PUBLICATIONS

Kano–Murakami et al., A rice homeotic gene, OSH1, causes unusual phenotypes in transgenic toabacco, 1993, FEBS, vol. 334, No. 3, pp. 365–368.*

McConnell et al., Role of PHABULOSA and PHAVOLUTA in determining radial patterning in shoots, Jun. 7, 2001, Nature, vol. 411, pp. 709–713.*

Finnegan et al., Transgene Inactivation: Plants Fight Back!, Sep. 12, 1994, Bio/Technology, pp. 883–887.*

Eshed et al., Establishment of polarity in lateral organs of plants, 2001, Current Biology, vol. 11, pp. 1251–1260.*

Bowie et al., Deciphering the Message in Protein Sequences: Tolerance to Amino Acid Substitutions, Mar. 16, 1990, Science, vol. 247, pp. 1306–1310.*

Watillon et al., Accession No. Z47076, Direct Submission.*

* cited by examiner

*Primary Examiner*—David T. Fox
*Assistant Examiner*—Stuart K. Baum
(74) *Attorney, Agent, or Firm*—Jacobson Holman PLLC

(57) ABSTRACT

This invention relates to a nucleic acid molecule encoding the catalytic subunit of a protein phosphatase (PP2AC-JD) that belongs to the PP2A family. The PP2AC-JD interacts with the phytochrome A, a primary photoreceptor in the light signal transduction in plants, in the photoperiodic control of flowering. The present invention also provides the methods and processes for generating transgenic higher plants transformed with said nucleic acid molecule to engineer flowing time of economically important crop plants.

6 Claims, 6 Drawing Sheets

```
  M   D   L   D   Q   W   I   S   K   V   K   D   G   Q   H   L   L   E    18
ATG GAT TTG GAC CAG TGG ATC TCG AAG GTT AAA GAC GGC CAA CAC CTT CTC GAA    54

D   E   L   Q   L   L   C   E   Y   V   K   E   I   L   I   E   E   S    36
GAC GAA CTT CAA CTT CTC TGC GAA TAT GTT AAA GAG ATT CTT ATT GAG GAG TCC   108

N   V   Q   P   V   N   S   P   V   T   V   C   G   D   I   H   G   Q    54
AAT GTG CAA CCT GTG AAT AGT CCA GTA ACT GTT TGT GGT GAT ATT CAT GGT CAG   162

F   H   D   L   M   K   L   F   Q   T   G   G   H   V   P   E   T   N    72
TTT CAT GAT CTA ATG AAA CTT TTC CAG ACC GGT GGT CAT GTT CCC GAG ACA AAT   216

Y   I   F   M   G   D   F   V   D   R   G   Y   N   S   L   E   V   F    90
TAC ATT TTT ATG GGG GAC TTT GTT GAT CGG GGT TAC AAT AGT CTT GAA GTA TTC   270

T   I   L   L   L   K   A   R   Y   P   A   N   I   T   L   L   R       108
ACC ATC CTT TTG CTT CTA AAA GCT AGA TAC CCG GCT AAT ATT ACC CTT CTA CGT   324

G   N   H   E   S   R   Q   L   T   Q   V   Y   G   F   Y   D   E   C   126
GGA AAT CAT GAA AGT AGA CAA CTC ACC CAG GTC TAT GGA TTT TAT GAT GAA TGC   378

Q   R   K   Y   G   N   A   N   A   W   R   Y   C   T   D   V   F   D   144
CAG AGA AAG TAT GGA AAT GCT AAT GCT TGG CGA TAC TGT ACC GAT GTC TTC GAC   432

Y   L   T   L   S   A   I   I   D   G   T   V   L   C   V   H   G   G   162
TAT CTT ACA CTT TCT GCA ATT ATA GAT GGA ACT GTG CTT TGT GTT CAC GGC GGC   486

L   S   P   D   I   R   T   I   D   Q   I   R   V   I   E   R   N   C   180
CTT TCT CCA GAC ATT CGA ACA ATT GAC CAG ATA AGA GTC ATT GAG CGG AAC TGT   540

E   I   P   H   E   G   P   F   C   D   L   M   W   S   D   P   E   D   198
GAA ATT CCT CAT GAG GGG CCA TTT TGT GAT CTA ATG TGG AGT GAT CCT GAG GAT   594

I   E   T   W   A   V   S   P   R   G   A   G   W   L   F   G   S   R   216
ATT GAA ACA TGG GCA GTC AGT CCG CGT GGA GCT GGT TGG CTT TTC GGA TCT CGG   648

V   T   S   E   F   N   H   I   N   N   L   D   L   V   C   R   A   H   234
GTT ACA TCT GAG TTC AAT CAC ATA AAC AAC CTT GAT CTT GTT TGT CGA GCA CAT   702

Q   L   V   Q   E   G   L   K   Y   M   F   Q   D   K   G   L   V   T   252
CAA CTT GTA CAA GAA GGC CTT AAA TAC ATG TTC CAA GAT AAA GGC CTT GTA ACT   756

V   W   S   A   P   N   Y   C   Y   R   C   G   N   V   A   S   I   L   270
GTA TGG TCT GCA CCT AAT TAC TGT TAC CGT TGT GGA AAT GTA GCT TCT ATT CTT   810

S   F   N   E   N   M   E   R   E   V   K   F   F   T   E   T   E   E   288
AGT TTC AAT GAA AAT ATG GAG AGA GAA GTT AAG TTT TTC ACT GAA ACA GAG GAG   864

N   N   Q   M   R   G   P   R   T   G   V   P   Y   F   L   *           304
AAC AAT CAG ATG AGA GGG CCA AGG ACA GGT GTT CCG TAT TTC TTA TAA           912
```

FIG. 1

```
PP2AC-1  --------MPSNGDLDRQIEQLMECKPLSEADVRTLCDQARAILVEEYNVQPVKCPVTVCGDIHGQFYDLIELFRIGGNAPDTNYLFMGDYVDRGYYSVETVSLLVALKVRYRD 106
PP2AC-2  --------MPLNGDLDRQIEQLMECKPLGEADVKILCDQAKAILVEEYNVQPVKCPVTVCGDIHGQFYDLIELFRIGGNAPDTNYLFMGDYVDRGYYSVETVSLLVALKVRYRD 106
PP2AC-5  --------MPPATGDIDRQIEQLMECKALSETEVKMLCEHAKTILVEEYNVQPVKCPVTVCGDIHGQFYDLIELFRIGGSSPDTNYLFMGDYVDRGYYSVETVSLLVALKVRYRD 107
PP2AC-3  MGANSIPTDATIDLDEQISQLMQCKPLSEQQVRALCEAKAKEILMDESNVQPVKSPVTICGDIHGQFHDLAELFRIGMCPDTNYLFMGDYVDRGYYSVETVTLLVALKMRYPQ 113
PP2AC-4  MGANSLPTDATLDLDEQISQLMQCKPLSEQQVRALCEKAKAKEILMDESNVQPVKSPVTICGDIHGQFHDLAELFRIGGCKPDTNYLFMGDYVDRGFYSVETVTLLVGLKVRYPQ 113
HumPPX1  --------MAEISDLDRQIEQLRRCELIKESEVKALCAKAREILVEESNVQRVDSPVTVCGDIHGQFYDLKELFRVGGDVPETNYLFMGDFVDRGFYSVETFLLLLALKVRYPD 106
RabPPX1  --------MAEISDLDRQIEQLLRCELIKESEVKALCAKAREILVEESNVQRVDSPVTVCGDIHGQFYDLKELFRVGGDVPETNYLFMGDFVDRGFYSVETFLLLLALKVRYPD 106
AtPPX-1  --------MSDLDRQIGQLKRCEPLSESEVKALCLKAMEILVEESNVQRVDAPVTLCGDIHGQFYMMELFKVGGDCPKTNYLFMGDFVDRGYYSVETFLLLLALKVRYPD 103
AtPPX-2  --------MSDLDKQIEQLKRCEALKESEVKALCLKAMEILVEESNVQRVDAPVTICGDIHGQFYDMKELFKVGGDCPKTNYLFLGDFVDRGYYSVETFLLLLKARHPA 103
ATPP2A1  --------MDLDQWISKVKDGQHLSEDELQLLCEYVKEILIEESNVQPVNSPVTVCGDIHGQFHDLMKLFQTGGHVPETNYIFMGDFVDRGYNSLEVFTILLLKARHPA 102
ATPP2A  --------MDLDQWISK KDGQHLSEDELCLLCEYVKEILIEESNVQPVNSPVTVCGDIHGQFHDLMKLFQTGGHVPDTNYIFMGDFVDRGYNSLEVFTILLLKARYPA 102
PP2ACJD --------MDLDQWISKVKDGQHLEDELQLLCEYVKEILIEESNVQPVNSPVTVCGDIHGQFHDLMKLFQTGGHVPETNYIFMGDFVDRGYNSLEVFTILLLKARYPA 102

PP2AC-1  RLTILRGNHESRQITQVYGFYDECLRKYGNANVWKYFTDLFDYLPLTALIESQVFCLHGGLSPSLDTLDNIRSLDRIQEVPHEGPMCDLLWSDPDD-RCGWGISPRGAGYTFG 218
PP2AC-2  RLTILRGNHESRQITQVYGFYDECLRKYGNANVWKYFTDLFDYLPLTALIESQVFCLHGGLSPSLDTLDNIRSLDRIQEVPHEGPMCDLLWSDPDD-RCGWGISPRGAGYTFG 218
PP2AC-5  RLTILRGNHESRQITQVYGFYDECLRKYGNANVWKHFTDLFDYLPLTALIESQVFCLHGGLSPSLDTLDNIRSLDRIQEVPHEGPMCDLLWSDPDD-RCGWGISPRGAGYTFG 219
PP2AC-3  RITILRGNHESRQITQVYGFYDECLRKYGMANVWKIFTDLFDYFPLTALVESEIFCLHGGLSPSIETLDNIRNFDRVQEVPHEGPMCDLLWSDPDD-RCGWGISPRGAGYTFG 225
PP2AC-4  RITILRGNHESRQITQVYGFYDECLRKYGNANVWKIFTDLFDFPLTALVESEIFCLHGGLSPSIETLDNIRNFDRVQEVPHEGPMCDLLWSDPDD-RCGWGISPRGAGYTFG 225
HumPPX1  RITLIRGNHESRQITQVYGFYDECLRKYGSVTVWRYCTEIFDYLSLSAIIDGKIFCVHGGLSPAINTLDQIRTIDRKQEVPHDGPMCDLLWSDPED-TTGWGVSPRGAGYLFG 218
RabPPX1  RITLIRGNHESRQITQVYGFYDECLRKYGSVTVWRYCTEIFDYLSLSAIIDGKIFCVHGGLSPSIQTLDQIRTIDRKQEVPHDGPMCDLLWSDPED-TTGWGVSPRGAGYLFG 218
AtPPX-1  RITLIRGNHESRQITQVYGFYDECLRKYGSNVWRYCTDIFDYMSLSLSAVVENKIFCVHGGLSPAIMTLDQIRTIDRKQEVPHDGAMCDLLWSDPEDIVDGWGLSPRGAGFLFG 216
AtPPX-2  RITLIRGNHESRQITQVYGFYDECLRKYGSVNVWRYCTDIFDYLSLSAIVENKIFCVHGGLSPAIMTLDQIRAIDRKQEVPHDGAMCDLLWSDPEDIVDGWGLSPRGAGFLFG 216
ATPP2-1  NITLLRGNHESRQLTQVYGFYDECQRKYGNANAWRYCTDVFDYLTLSAIIDGTVLCVHGGLSPDVRTIDQIRLIERNCEIPHEGPFCDLMWSDPED-IETWAVSPRGAGWLFG 214
ATPP2-3  NITLLRGNHESRQLTQVYGFYDECQRKYGNANAWRYCTDVFDYLTLSAIIDGTVLCVHGGLSPDVRTIDQIRLIERNCEIPHEGPFCDLMWSDPED-IETWAVSPRGAGWLFG 214
PP2ACJD NITLLRGNHESRQLTQVYGFYDECQRKYGNANAWRYCTDVFDYLTLSAIIDGTVLCVHGGLSPDIRTIDQIRVIERNCEIPHEGPFCDLMWSDPED-IETWAVSPRGAGWLFG 214

PP2AC-1  QDIAAQFNHNNGLSLISRAHQLVMEGFNWCQDKN-VVTVFSAPNYCYRCGNMAAILEIGENMEQNFLQFDPAPRQVEPDTTRKT-PDYFL 306
PP2AC-2  QDIATQFNHNNGLSLISRAHQLVMEGYNWCQEKN-VVTVFSAPNYCYRCGNMAALLEIGENMEQNFLQFDPAPRQVEPDTTRKT-PDYFL 306
PP2AC-5  QDIATQFNHTNGLSLISRAHQLVMEGFNWCQEKN-VVTVFSAPNYCYRCGNMAAILEIGENMDQNFLQFDPAPRQVEPTTRKT-PDYFL 307
PP2AC-3  QDISEQFNHTNNLKLIARAHQLVMDGYNWAHEQK-VVTIFSAPNYCYRCGNMASILEVDDCRNHTFIQFEAPRRGEPDVTRRT-PDYFL 313
PP2AC-4  QDISEQFNHTNNLKLIARAHQLVMDGFNWAHEQK-VVTIFSAPNYCYRCGNMASILEVDDCRNHTFIQFEAPRRGRPDVTRRT-PDYFL 313
HumPPX1   QFNAAN IM CRAHQLVMEGYKWHFNET-VLTVWSAPNYCYRCGNVAAILELDEHLQKDF IFEAAPQETRGIPSKKPVADYFL 307
RabPPX1   QFNAAN IM CRAHQLVMEGYKWHFNET-VLTVWSAPNYCYRCGNVAAILELDEHLQKDF IFEAAPQETRGIPSKKPVADYFL 307
AtPPX-1   GSVVTSFNHSNNIDYIARAHQLVMEGYKWHFDSQ-IVTVWSAPNYCYRCGNVASILELDENLNKEFRVDAAQQDSRGPPAKKAPDYFL 305
AtPPX-2  GSVVTSFNHSNNIDYICRAHQLVMEGYKWHFNSQ-IVTVWSAPNYCYRCGNVASILELDENLNKEFRVEDAAPQESRGALAKKAPDYFL 305
ATPP2-1  SRVTEFNHINNLDLVCRAHQLVQEGLKYMFQDKGLVTVWSAPNYCYRCGNVASILSFNDMEREVKFTETEENNQMRGPRTGV-PYFL 303
ATPP2-3  SRVTEFNHINNLDLVCRAHQLVQEGLKYMFQDKGLVTVWSAPNYCYRCGNVASILSFNDMEREVKFTETEENNQMRGPRTGV-PYFL 303
PP2ACJD SRVTSEFNHINNLDLVCRAHQLVQEGLKYMFQDKGLVTVWSAPNYCYRCGNVASILSFNEMEREVKFTETEENNQMRGPRTGV-PYFL 303
```

FIG. 2

Figure 4. Tissue-specific expression of *PP2A-JD* gene
A. Light dependence
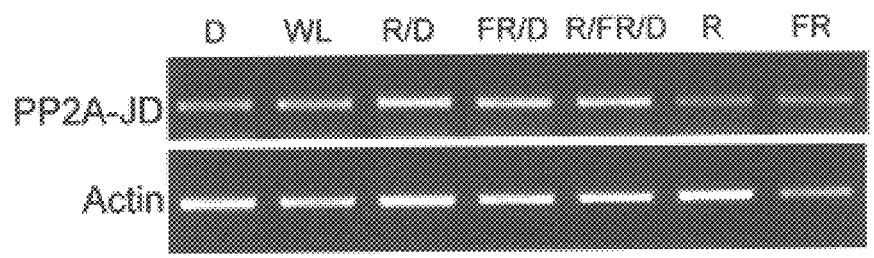
B. Tissue-specific expression
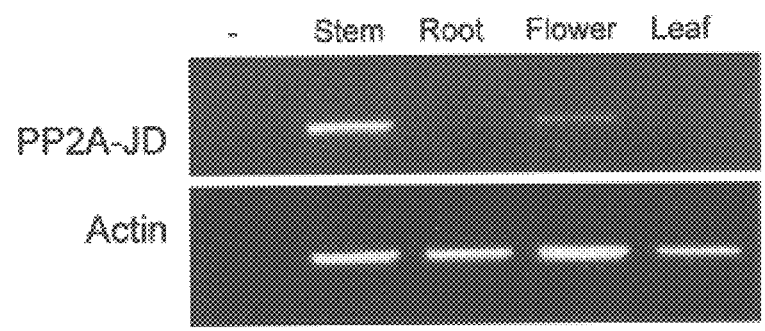

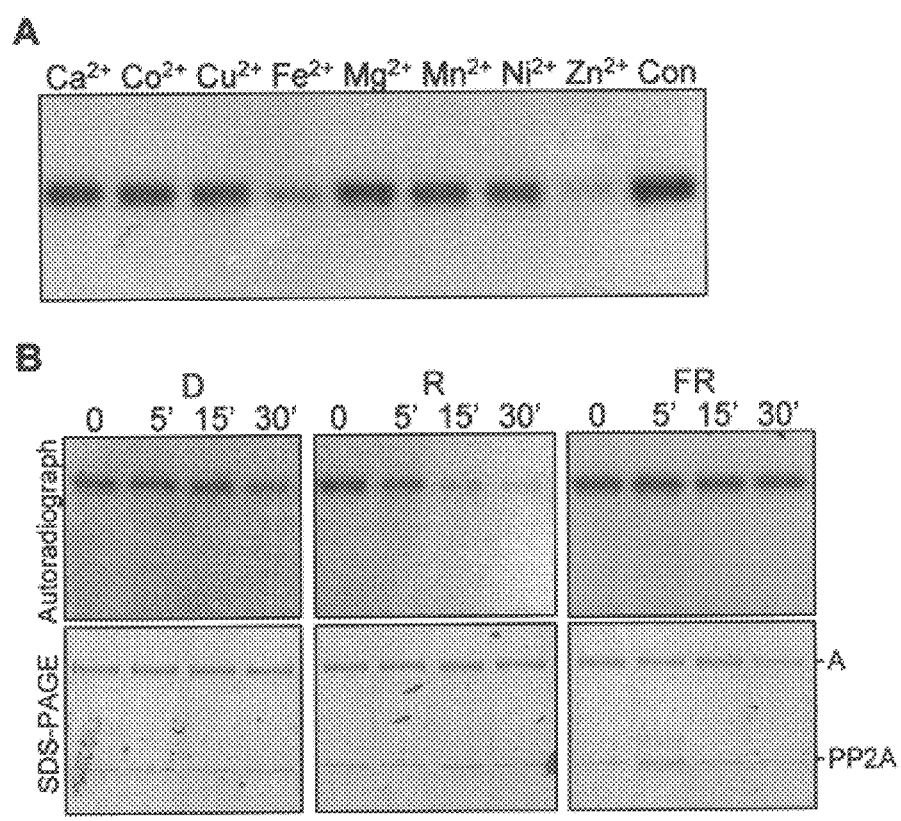
Figure 5. Dephosphorylation of phytochrome A by PP2AC-JD

Figure 6. Transgenic *Arabidopsis* Plants
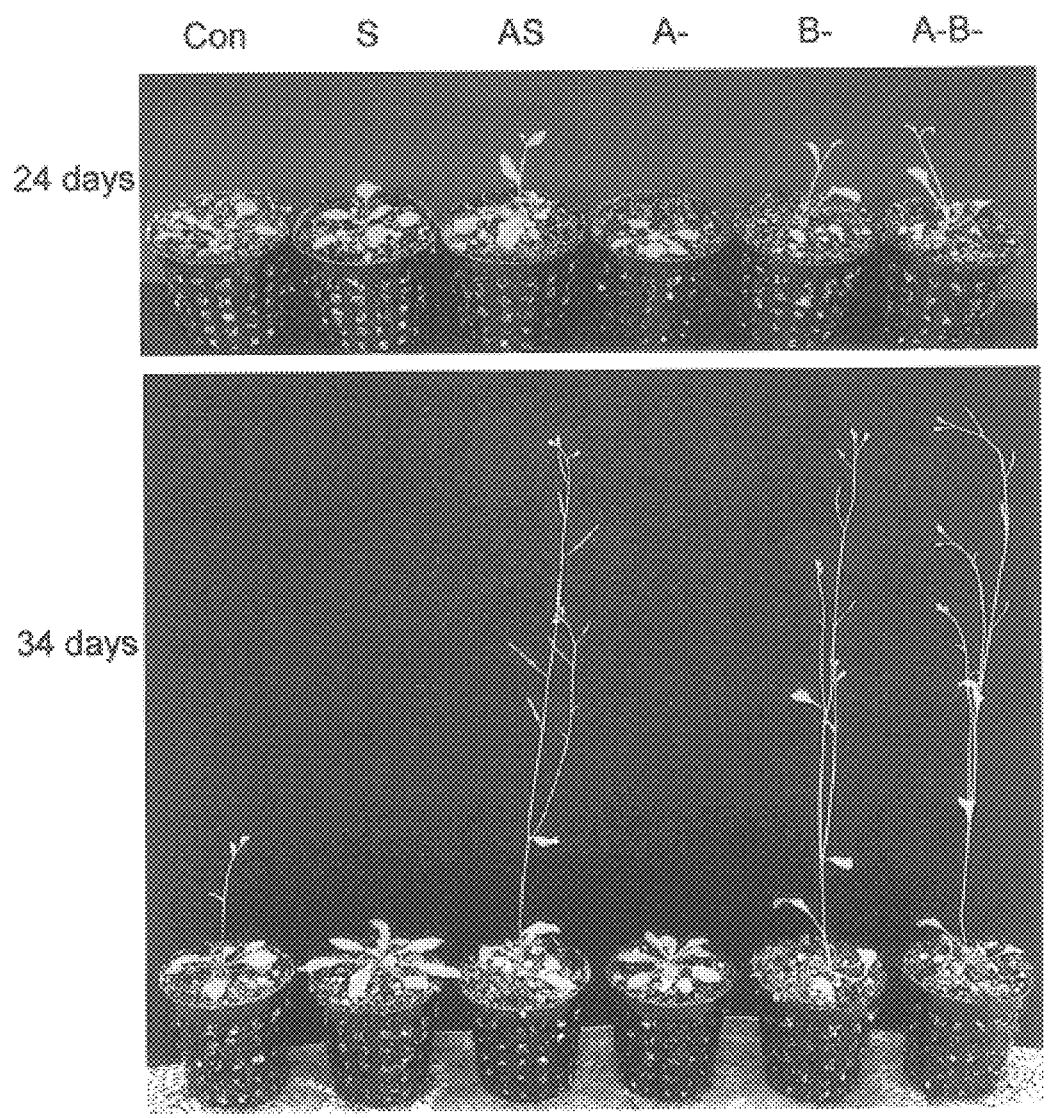

SEQUENCE LISTING

<160> NUMBER OF SEQ ID NOS: 4

<210> SEQ ID NO 1
<211> LENGTH: 912
<212> TYPE: DNA
<213> ORGANISM: Pisum sativum

<400> SEQUENCE: 1

```
atggatttgg accagtggat ctcgaaggtt aaagacggcc aacaccttct cgaagacgaa      60
cttcaacttc tctgcgaata tgttaaagag attcttattg aggagtccaa tgtgcaacct     120
gtgaatagtc cagtaactgt ttgtggtgat attcatggtc agtttcatga tctaatgaaa     180
```

-continued

```
cttttccaga ccggtggtca tgttcccgag acaaattaca ttttatggg ggactttgtt      240 gatcggggtt acaatagtct tgaagtattc accatccttt tgcttctaaa agctagatac      300
ccggctaata ttaccttct acgtggaaat catgaaagta gacaactcac ccaggtctat       360
ggattttatg atgaatgcca gagaaagtat ggaaatgcta atgcttggcg atactgtacc      420
gatgtcttcg actatcttac actttctgca attatagatg gaactgtgct ttgtgttcac      480
ggcggccttt ctccagacat tcgaacaatt gaccagataa gagtcattga gcggaactgt      540
gaaattcctc atgaggggcc attttgtgat ctaatgtgga gtgatcctga ggatattgaa      600
acatgggcag tcagtccgcg tggagctggt tggcttttcg gatctcgggt tacatctgag      660
ttcaatcaca taaacaacct tgatcttgtt tgtcgagcac atcaacttgt acaagaaggc      720
cttaaataca tgttccaaga taaaggcctt gtaactgtat ggtctgcacc taattactgt      780
taccgttgtg gaaatgtagc ttctattctt agtttcaatg aaaatatgga gagagaagtt      840 aagttttca ctgaaacaga ggagaacaat cagatgagag ggccaaggac aggtgttccg       900
tatttcttat aa                                                          912
```

<210> SEQ ID NO 2
<211> LENGTH: 303
<212> TYPE: PRT
<213> ORGANISM: Pisum sativum

<400> SEQUENCE: 2

```
Met Asp Leu Asp Gln Trp Ile Ser Lys Val Lys Asp Gly Gln His Leu
  1               5                  10                  15

Leu Glu Asp Glu Leu Gln Leu Leu Cys Glu Tyr Val Lys Glu Ile Leu
             20                  25                  30

Ile Glu Glu Ser Asn Val Gln Pro Val Asn Ser Pro Val Thr Val Cys
         35                  40                  45

Gly Asp Ile His Gly Gln Phe His Asp Leu Met Lys Leu Phe Gln Thr
     50                  55                  60

Gly Gly His Val Pro Glu Thr Asn Tyr Ile Phe Met Gly Asp Phe Val
 65                  70                  75                  80

Asp Arg Gly Tyr Asn Ser Leu Asp Val Phe Thr Ile Leu Leu Leu Leu
                 85                  90                  95

Lys Ala Arg Tyr Pro Ala Asn Ile Thr Leu Leu Arg Gly Asn His Glu
            100                 105                 110

Ser Arg Gln Leu Thr Gln Val Tyr Gly Phe Tyr Asp Glu Cys Gln Arg
        115                 120                 125

Lys Tyr Gly Asn Ala Asn Ala Thr Arg Tyr Cys Thr Asp Val Phe Asp
    130                 135                 140

Tyr Leu Thr Leu Ser Ala Ile Ile Asp Gly Thr Val Leu Cys Val His
145                 150                 155                 160

Gly Gly Leu Ser Pro Asp Ile Arg Thr Ile Asp Gln Ile Arg Val Ile
                165                 170                 175

Glu Arg Asn Cys Glu Ile Pro His Glu Gly Pro Phe Cys Asp Leu Met
            180                 185                 190

Trp Ser Asp Pro Glu Asp Ile Glu Thr Trp Ala Val Ser Pro Arg Gly
        195                 200                 205

Ala Gly Trp Leu Phe Gly Ser Arg Val Thr Ser Glu Phe Asn His Ile
    210                 215                 220
```

-continued

```
Asn Asn Leu Asp Leu Val Cys Arg Ala His Gln Leu Val Gln Glu Gly
225                 230                 235                 240

Leu Lys Tyr Met Phe Gln Asp Lys Gly Leu Val Thr Val Trp Ser Ala
            245                 250                 255

Pro Asn Tyr Cys Tyr Arg Cys Gly Asn Val Ala Ser Ile Leu Ser Phe
                260                 265                 270

Asn Glu Asn Met Glu Arg Glu Val Lys Phe Phe Thr Glu Thr Glu Glu
        275                 280                 285

Asn Asn Gln Met Arg Gly Pro Arg Thr Gly Val Pro Tyr Phe Leu
    290                 295                 300

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: 5'
      primer for PP2AC-JD cDNA

<400> SEQUENCE: 3
cgcgaattcg atttggacca gtggatc                                              27

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: 3' primer
      for PP2AC-JD cDNA

<400> SEQUENCE: 4
cgcctcgagt aagaaatacg gaacacctc                                            29
```

NUCLEIC ACID MOLECULE ENCODING THE CATALYTIC SUBUNIT OF A PROTEIN PHOSPHATASE 2A THAT REGULATES FLOWERING TIME IN PLANTS

BACKGROUND OF THE INVENTION

This invention relates to a nucleic acid molecule encoding the catalytic subunit of a protein phosphatase (PP2AC-JD) that belongs to the PP2A family. The PP2AC-JD interacts with the phytochrome A, a primary photoreceptor in the light signal transduction in plants, in the photoperiodic control of flowering. The present invention also provides the methods and processes for generating transgenic higher plants transformed with said nucleic acid molecule to engineer flowering time of economically important crop plants.

The present invention is to provide a nucleic acid molecule encoding the catalytic subunit of a protein phosphatase 2A that dephosphorylates the phytochrome photoreceptors and has a role in the photoperiodic control of flowering time in plants, the methods and processes required for generating and analyzing biologically active polypeptides encoded by the nucleic acid molecule in enzymatic and biochemical assays, and the molecular ways for generating transgenic higher plants that exhibit delayed or accelerated flowering.

Plant flowering is regulated through complex interactions between intrinsic developmental factors and various environmental cues (Blázquez, 2000). The intrinsic factors include genes involved in the timing of flowering, flower meristem identity, and flower organ identity. Environmental cues that play critical roles in the flowering control are light, temperature, and water. Plant responses to these environmental cues appear in the forms of photoperiodism and vernalization in many cases (Izawa et al., 2000). Most of the signaling pathways that regulate flowering time and flower architecture have been elucidated by genetic analyses of mutant plants affected in a variety of aspects in flowering, and some of them, such as LEAFY and photoreceptors (Izawa et al., 2000; Reed et al., 2000; Weigel, et al., 1992), were molecular biologically and biochemically investigated in detail. A currently accepted model for the control of flowering in Arabidopsis depicts that there are four major signaling pathways, each mediated by light, gibberellic acid (GA), temperature, and circulating sucrose (Blázquez, 2000). Under the long day condition, light signals perceived by the photoreceptors trigger the activation of a facultative long day pathway in which the "clock-related" genes, such as ELF3, TOC1, LHY, CCA1, FKF1, and ZTL, are involved (Blázquez, 2000). However under the short day condition, flowering is exclusively regulated by light-independent signaling pathways that are mediated primarily by GA and temperature. The circulating sucrose, an indicator for the metabolic state of plants, also regulates flowering.

Light effects on the flowering are collectively called as photoperiodism, the lengths of alternating day and night. Based on the photoperiodic flowering responses, plants can be classified as two major categories; the short day plants that flower only in short days and the long day plants whose flowering occurs only in long days or activated by the long day condition, although some plants are day-neutral. At least two photoreceptors, the red and far-red light absorbing phytochromes and the blue light absorbing cryptochromes, are known to participate in the photoperiodic control of flowering in plants (Devlin and Kay, 2000; Mockler et al., 1999). The red light is perceived by the phytochrome B and eventually regulates the CONSTANS gene expression, whose gene product is a zinc finger transcription factor that regulates the transcription of the floral meristem identity genes (Blázquez, 2000). The far-red and blue lights are perceived by the phytochrome A and the cryptochromes, respectively, and regulate the expression of "clock" genes, such as ELF3, TOC1, LHY, CCA1, and ZTL, in the facultative pathway (Blázquez, 2000; Reed et al., 2000). The two light signaling pathways are eventually integrated by the CONSTANS transcription factor. Furthermore the light signals also interact with the GA-dependent pathway, especially under the short day condition (Blázquez, 2000).

Recent accumulating evidences suggest that the phytochromes and cryptochromes do not function independently but interact with each other in the flowering control (Guo et al., 2001; Más et al., 2000; Mockler et al., 1999). The cryptochromes 1 and 2 (CRY1 and CRY2) are phosphorylated by the phytochrome kinases. The CRY1 and CRY2 interact with the phytochrome A (Ahmad et al., 1998), and the CRY2 with the phytochrome B in vitro. A $Ca^{2+}$-binding protein, Arabidopsis SUB1, plays a role in the cryptochrome-phytochrome coaction (Guo et al., 2001). These interactions between the phytochromes and cryptochromes have also been functionally confirmed using mutant plants. These observations entail that a counter-acting partner to the phytochrome kinases, a protein phosphatase, would be involved in these interactions. In addition, based on the reversible phosphorylation of proteins in various signaling cascades in animals and plants (Palczewski et al., 1982; Stone et al., 1995), the presence of a protein phosphatase activity has been frequently implicated in the phytochrome-mediated light signal transduction during the photomorphogenesis, including the flowering control. However no such protein phosphatase gene has been identified so far.

In the present invention, we carried out a yeast two-hybrid screen using the C-terminal domain of the Arabidopsis phytochrome A as bait and a pea cDNA library to identify functional partners that specifically interact with the phytochrome A. One of the major positive clones isolated was a gene encoding the catalytic subunit of a protein phosphatase (designated PP2AC-JD in the invention) that belongs to the protein phosphatase 2A (PP2A) family (Virshup, 2000). The PP2AC-JD gene was exclusively expressed in the flower and stalk organs in a light-independent way. A recombinant PP2AC-JD protein expressed in *E. coli* expression system efficiently dephosphorylated the phosphorylated oat phytochrome A in the presence of $Fe^{2+}$or $Zn^{2+}$. The Pfr phytochrome was a better substrate for the PP2AC-JD than the Pr form. Transgenic Arabidopsis plants overexpressing the sense PP2A-JD gene flowered later than control plants, like a phytochrome A-deficient mutant plant. On the contrary, those with an anti-sense PP2AC-JD transgene flowered earlier with a time course similar to that observed in a phytochrome B-deficient mutant plant. These results indicate that the PP2AC-JD regulates the flowering time, possibly via the phytochrome-mediated light signal transduction pathway. This invention can be practically applied to control flowering time of higher plants economically important in agriculture and horticulture.

With rapidly accumulating technological information in recent years in the field of tissue culture and genetic transformation in plants, a gene of interest can now be routinely introduced into any desired plants with practical aims to enhance commercial value, yields, and environmental adaptability. For example, flowering plants can be engineered so that they flower earlier than control plants without any detrimental phenotypic effects. Furthermore the present invention can be applied to redistribute more metabolic nutrients into the vegetative organs than into the flowers by delaying flowering time, potentially resulting in improved productivity.

As used herein, the term "economically important higher plants" refers to higher plants that are capable of photosynthesis and widely cultivated for commercial purpose. The term "plant cell" includes any cells derived from a higher plant, including differentiated as well as undifferentiated tissues, such as callus and plant seeds.

SUMMARY OF THE INVENTION

The present invention relates to nucleic acid molecules encoding the catalytic subunit of a protein phosphatase with structural and functional characteristics typical of the PP2A family. Such nucleic acid molecules preferentially encode a protein with the amino acid sequence as given in SEQ ID NO: 2 or fragments thereof that possess the enzymatic activity of the above-described protein phosphatase. The PP2AC-JD physically interacts with the C-terminal domain of the phytochrome A. It dephosphorylates the phytochrome A in vitro, preferentially the Pfr form, in the presence of $Fe^{2+}$ or $Zn^{2+}$, a typical biochemical feature of the PP2A family (Virshup, 2000).

The present invention also relates to nucleic acid molecules that hybridize under high stringent conditions to a nucleic acid molecule as given in SEQ ID NO: 1. The term "hybridize under high stringent conditions" means that such nucleic acid molecules hybridize through complementary base pairing under conventional hybridization conditions.

Also, provided includes an uninterrupted gene sequence encoding the PP2AC-JD, a nucleic acid fragment that can be directly ligated into recombinant DNA constructs, and the PP2AC-JD expression vectors that can be readily used to transform cells of higher plants according to the present invention.

The present invention relates to a polypeptide or biologically active fragments of such a polypeptide encoded by said nucleic acid molecules to be used for enzymatic analysis. The protein phosphatase encoded by said nucleic acid molecules exhibits a dephosphorylating activity that is specific to the phytochrome dephosphorylation in a $Fe^{2+}$ or $Zn^{2+}$-dependent way. Furthermore, the invention describes a polypeptide or biologically active fragments of such a polypeptide functionally expressed in bacterial cells. The polypeptide encoded by the above-described nucleic acid molecules shares common structural and functional properties with the catalytic subunit of the PP2A family.

Provided also are transgenic higher plants, especially flowering plants, that are readily accessible to the Agrobacterium-mediated transformation. Overexpression or anti-sense suppression of the PP2AC-JD gene results in delayed or early flowering, respectively. These phenotypic traits can be exploited in a way that higher plants of interest harboring the PP2AC-JD gene exhibit delayed or accelerated flowering, a very important commercial trait in horticulture and agriculture.

Therefore, the present invention provides: 1. Nucleic acid molecules encoding a polypeptide that dephosphorylates the phytochrome kinases in plants, comprising a nucleotide sequence as given in SEQ ID NO: 1. 2. *Escherichia coli* BL21 PP2AC-JD cells (KCTC 1003BP), containing a nucleic acid molecule with the nucleotide sequence as given in SEQ ID NO:1, which is deposited at the Korean Collection for Type Cultures as International Depositary Authority on May 11, 2001 under Budapest Treaty.

BRIEF DESCRIPTION OF THE DRAWINGS

FIG. 1 shows the nucleotide sequence of a pea cDNA clone (GenBank Accession No.: AF305635) and the deduced amino acid sequence. The cDNA consists of 912 bases, including the start and stop codons. It encodes the catalytic subunit of a protein phosphatase (designated PP2AC-JD in the invention) that consists of 303 amino acids with a predicted molecular mass of 34.7 kDa.

FIG. 2 shows a multiple sequence alignment of the deduced amino acid sequences of the PP2A-JD and related protein phosphatases from animals and plants. The sequences were extracted from GenBank. Gaps were introduced to maximize sequence homologies between them. The amino acid sequences were aligned using the PIMA 1.4 program (Baylor College of Medicine, Houston Tex.). The sequences aligned included the catalytic subunits of the PP2A family members (PP2AC-1 to -5) from Arabidopsis, human and rat PPX1s, Arabidopsis PPX1 and -2, and two Arabidopsis PP2A homologues with 98% homologies to the PP2AC-JD protein. It is evident that the PP2AC-JD forms a distinct subfamily with the two Arabidopsis PP2A homologues. The protein phosphatases aligned are; PP2AC-1 (Q07098), PP2AC-2 (Q07099), PP2AC-3 (Q07100), PP2AC-4 (P48578), PP2AC-5 (O04951), AtPPX-1 (S42558), AtPPX-2 (P48528), human PPX1 (S28173), rat PPX1 (AAA41930), ATPP2A1 (AAD50050), ATPP2A3 (BAB03163), and PP2AC-JD (AF305635, this work).

FIG. 4 shows the expression pattern of the pea PP2AC-JD gene. (A) Light effect. Pea plants were grown under various light conditions for 6 days, and total RNAs were isolated and subject to reverse transcriptase-mediated PCR (RT-PCR) runs. Note that there was no light effect under all light conditions tested. (B) Organ-specific expression. Pea plants were grown in the light for 10 days, and total RNAs were separately isolated from leaves, stems, and roots and subject to RT-PCR analysis. A pea actin gene was used as a marker for constitutive expression under the given growth condition. Note that the PP2AC-JD gene is expressed exclusively in the flower and stalk organs.

FIG. 5 shows the dephosphorylation of the phosphorylated oat phytochrome A by the PP2AC-JD protein. The oat phytochrome A was first autophosphorylated in the presence of γ[32P]ATP under the light conditions indicated. The recombinant PP2AC-JD protein was expressed via the pGEX-4T-1 expression vector in *E. coli* strain BL21 as a GST fusion, and the GST tag domain was cleaved out by thrombin digestion. (A) Cation requirements for the PP2AC-JD activity. One μg of the phosphorylated phytochrome A was incubated with 0.2 μg of the recombinant PP2AC-JD for 30 minutes at room temperature, analysed on 12% SDS-PAGE, and subject to autoradiography. (B) Spectral form-dependent dephosphorylation of the phytochrome A. The Pfr form was a better substrate for the PP2AC-JD than the Pr form.

FIG. 6 shows the transgenic Arabidopsis plants transformed with a sense or an anti-sense PP2AC-JD gene sequence. The transgenic plants were grown in the long day condition for 24 days (A) or for 34 days (B) after germination. S; Sense orientation, AS; anti-sense orientation, Con; control plant transformed with the original vector alone.

Figure 3:
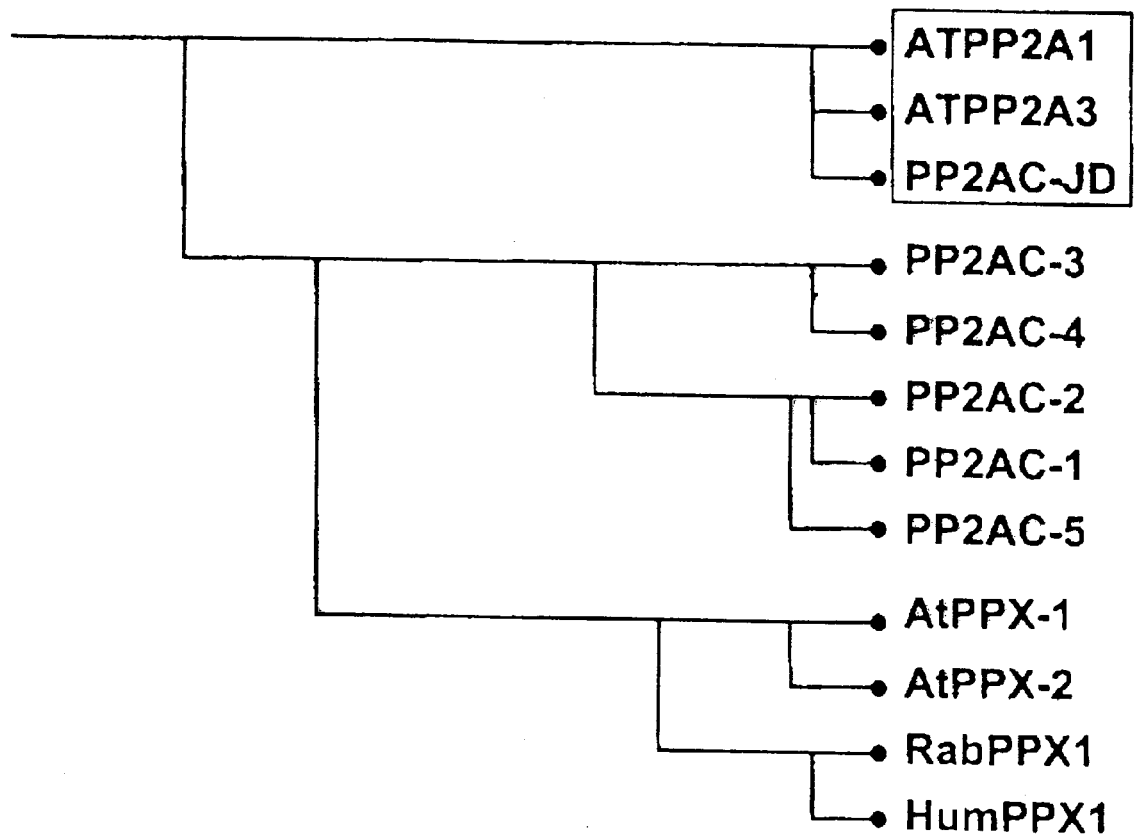
FIG. 3 shows a phylogenetic tree of the PP2A family members that were aligned in FIG. 2. It is evident that the PP2AC-JD forms a distinct subfamily with the ATPP2A1 and ATPP2A3. The three members share a 98% sequence identity, strongly suggesting that the two Arabidopsis PP2As are PP2AC-JD homologues.

Mutant plants that are deficient in either phytochrome A (A⁻), in phytochrome B (B⁻) or in both phytochromes A and B (A⁻B⁻) were also grown in the same experimental condition. Note that the sense transgenic plant exhibited delayed flowering, like the A⁻ plant. On the contrary, the anti-sense transgenic plant flowered earlier like the B⁻ plant. It is notable that the sense transgenic plants had larger leaves than control plants as observed in the A⁻ plant.

DETAILED DESCRIPTION OF THE INVENTION

Flowering is an important agronomic trait in horticulture and agriculture. As a result it has long been a target for genetic engineering with an aim to engineer flowering time and flower architecture. Flowering is regulated by a group of genes involved in flowering time, flower meristem identity, and flower organ identity as well as by various environmental cues. Light is one of the most important environmental factors that regulate flowering. It is now well established that at least two different photoreceptors, the red and far-red light absorbing phytochromes and the blue light absorbing cryptochromes, play critical roles in flowering. The recent observation that the cryptochromes are phosphorylated by the phytochrome kinases and the diverse roles of the reversible phosphorylation of proteins in various cellular processes suggested that a protein phosphatase activity may be required for the phytochrome-cryptochrome interaction.

Therefore the present invention provides nucleic acid molecules encoding the catalytic subunit of a protein phosphatase that belongs to the PP2A family. The nucleic acid molecules preferentially encode a protein with the amino acid sequence as given in SEQ ID NO: 2 or fragments thereof that possess the dephosphorylating activity of the above-mentioned protein phosphatase. Such a nucleic acid molecule as given in SEQ ID NO: 1 is more preferred. Furthermore, the invention relates to the plasmids and expression cassettes comprising nucleic acid molecules containing the nucleotide sequences as given in SEQ ID NO: 1 for functional expression in prokaryotic and eukaryotic cells. The nucleic acid molecule can be isolated as a full-size cDNA clone by various conventional methods, such as RT-PCR using the mRNA or through the screening of a cDNA library, well known techniques to the art. For the RT-PCR method, the poly(A)⁺ mRNA can be first converted into a primary cDNA using reverse transcriptase and the oligo(dT)$^{16-18}$ as the primer. An uninterrupted double stranded cDNA can then be synthesized by PCR using a pair of specific primers and the primary cDNA as template.

The present invention also relates to nucleic acid molecules that hybridize under high stringent conditions to a nucleic acid molecule as given in SEQ ID NO: 1. The term "hybridize under high stringent conditions" depicts that such nucleic acid molecules hybridize via complementary base pairing under conventional hybridization conditions, as described in Sambrook et al., (Molecular Cloning: A Laboratory Manual, $2^{nd}$ Ed., Cold Spring Harbor Laboratory, Cold Spring Harbor, N.Y., 1989). Nucleic acid molecules that hybridize with the above nucleic acid molecule include in general those from any higher plants, preferentially from plants of interests in horticulture and agriculture. To isolate a nucleic acid molecule that hybridize to the nucleic acid molecule as given in SEQ ID NO: 1, a cDNA or a genomic DNA library is screened using the the-above described nucleic acid molecule as probe, a molecular biological technique well known to the art.

According to the present invention, the term "degenerate" means that the nucleotide sequences of nucleic acid molecules are different from the above-described nucleic acid molecules in one or more base positions and highly homologous to said nucleic acid molecules. "Homologous" indicates a nucleotide sequence identity of at least 70% or higher. The term also includes derivatives of the nucleic acid molecules as described above generated by insertions, deletions, base substitutions, and recombinations. The "homologous" also describes that the nucleic acid molecules or the polypeptides encoded by said nucleic acid molecules are structurally and functionally equivalent.

Furthermore, the present invention relates to a polypeptide or biologically active fragments of such a polypeptide encoded by said nucleic acid molecule for the use in the enzymatic analysis and biochemical assays. One efficient way to get such a polypeptide is to use the recombinant expression systems. To do that, the nucleic acid molecule is first inserted into an expression vector containing regulatory elements, such as promoters, terminators, and polyadenylaton signals, required for efficient expression of the polypeptide encoded by said nucleic acid molecule. The expression cassettes are then transfected into appropriate host cells. The host cells can be either prokaryotic or eukaryotic. For efficient isolation of the expressed polypeptide from the host cell culture, affinity tags are attached to the N- or C-terminus of the polypeptide. The affinity tags can be easily removed from the fusion proteins after isolation by enzymatic or biochemical methods, a recently well-established technique to the art.

The enzymatic activity of the protein phosphatase encoded by said nucleic acid molecule can be assayed using a phosphorylated protein, preferentially autophosphorylated phytochromes. The reaction mixture is then analyzed on SDS-PAGE and visualized by autoradiography.

In one aspect, the protein phosphatase encoded by said nucleic acid molecule in the present invention specifically dephosphorylates the phytochrome kinases in the presence of $Fe^{2+}$ and $Zn^{2+}$.

The present invention can be applied to develop transgenic plant cells and plants containing said nucleic acid molecules with delayed or early flowering phenotypes. It is especially possible to redistribute metabolic nutrients preferentially into the vegetative tissues, such as leaves, stems, and roots, to improve productivity. Technical procedures for the development of such transgenic plant cells and plants are well known to the art.

EXAMPLES

Plant Materials and Growth Conditions

Seeds of pea plant was germinated and grown under sterile condition on the Murasbige and Skoog (MS) media. The *Arabidopsis thaliana* ecotype Columbia (Col-0) was grown on 0.5×MS medium. All Arabidopsis cultures were maintained in a controlled environment culture room at 26° C., 70% humidity and for the photoperiod of 16 hours. The Arabidopsis transformation was performed according to the simplified floral dip method, a well known technique to the art.

Enzymatic Treatments of DNA

DNA manipulations were carried out according to the standard procedures with some modifications whenever required. Restriction enzyme digestions were routinely done in 20 µl reaction volumes with an enzyme of 1–5 units per microgram DNA, and the mixtures were incubated at an appropriate temperature for 1–2 hours. Restriction enzyme digestion buffers used were those supplied by the manufacturer for each particular enzyme, unless specified otherwise. For ligation reactions, DNA fragments, either a digestion mixture or a PCR product, were first separated on 0.8–1.5% agarose gels, depending on the sizes of the DNA fragments of interest, and the desired DNA fragment was purified from the gel piece using either the GENECLEAN II Kit (BIO 101, Vista, USA) or the Gel Extraction Kit (Omega Biotek, Doraville, USA). Ligations were performed usually at the molar ratio of 1:1 to 1:3 in a 10 μl volume using the buffer supplied by the manufacturer, and the mixture was incubated at 13–16° C. for 10 minutes (for sticky-end ligations) or 30 minutes (for blunt-end ligations). T4 DNA ligase and its corresponding ligase buffer (NEB, Beverly, Mass., USA) were routinely used with 5–10 units of ligase in a 10 μl volume reaction. Polymerase chain reaction (PCR) was usually carried out 25 cycles, each with 1 minute denaturation at 94° C., 1 minute annealing at 60° C., and polymerization at 72° C. for 2 minutes per 1000 bases using the Pfu polymerase. For quantitative analysis, PCR was run 15–20 cycles, depending the gene expression levels, using the Taq polymerase (Promega, Madison, Wis.).

E. coli Transformation

For general cloning purpose, E. coli strain XL1-blue was routinely used as host cells for the transformation with plasmid DNAs. The competent E. coli cells were prepared in the laboratory and usually had an efficiency of 5×10$^{-6}$ to 10$^{-7}$ colonies per ptg control vector DNA. Three to five microliter of the ligation mixture was usually used to transform 100 μl of the competent E. coli cells. After incubation on ice for 20 minutes, the cell-DNA mixture was heat-shocked at 42° C. for 1 minute, and 1 ml of SOC medium was added. The mixture was then gently rotated at 37° C. for 1 hour to render the cells recovered from damage, and 50–300 μl was spread on LB plates containing an appropriate antibiotic. The plates were incubated at 37° C. overnight or until positive colonies were visible. For expression purpose, the E. coli strain BL21 and pGEX-4T-1 vector system were used (NEB).

Plasmid Isolation and Purification

Vector DNA was isolated routinely by the alkaline-SDS method from E. coli culture. A 1 ml (for high copy number plasmid) or a 10 ml LB-ampicillin culture (for low copy number plasmid) was routinely prepared for the small scale purification of plasmid DNA. For the large scale purification, TB medium (Terrific broth, 47.6 grams of TB mix per liter, Difco, Detroit, USA) which gives higher plasmid DNA yields, instead of LB medium, was used. To prepare plasmid DNA for DNA sequencing and Agrobacterium transformation, those isolated by the alkaline-SDS method was further purified using the Plasmid Miniprep Kit II (Omega Biotek, Seoul, KOREA).

Yeast Two-Hybrid Screen

Yeast two-hybrid screen was carried out using the MATCHMAKER Two-Hybrid System (Clonetech). A nucleotide sequence encoding the C-terminal domain (residues of 667–1122) of the Arabidopsis phytochrome A was cloned into the bait plasmid pGBT9, resulting in the pGB-phyA. In this vector construct, the phytochrome A gene is in frame fused to the nucleotide sequence encoding the GAL4 DNA binding domain, and the fusion protein is expressed under the control of the alcohol dehydrogenase gene (ADH1) promoter. A pea cDNA library was constructed from 5 day-old dark-grown seedlings. To construct the cDNA library, about 10 grams of plant material was homogenized in 20 ml of GTC buffer (4M GTC, 50 mM Tris.Cl, pH7.5, 10 mM EDTA, 5 mM Sodium acetate, 0.1 M 2-mercaptoethanol) supplemented with 1 ml PVP and 1 ml of 10% Sarcosyl. The homogenate was divided into two Falcon tubes and 0.1 volume of 2M sodium acetate (pH4.0) was added to each tube. After vigorous shaking with 1 volume of the phenol:chloroform:isoamyl alcohol (25:24:1), it was centrifuged at 10,000×g for 15 minutes at 20° C., and the supernatant was mixed with NaCl at a final concentration of 2M and further incubated at room temperature for 30 minutes. Total RNA was precipitated with 0.8 volume of ice-cold isopropanol at −20° C. overnight. RNA was then recovered by centrifugation and reprecipitated three times with 4M LiCl to remove carbohydrates. The total RNA pellet was rinsed with 70% ethanol two times and dried. The poly(A)$^+$ mRNA was isolated from total RNA using the Oligotex mRNA Spin Column (Qiagen) as described by the manufacturer. The cDNA was synthesized using the cDNA Synthesis Kit (Stratagene, La Jolla, USA) and cloned into the pAD-GAL4-2.1 phagemid vector using the HybriZAP-2.1 Two-Hybrid Predigested Vector/Gigapack Cloning Kit (Stratagene, La Jolla, Calif.). The average size of the cDNA inserts was about 1.5 kbp, and the primary library size was 1.25×10$^6$ pfa. The pGB-phyA bait plasmid was first transformed into the yeast strain HF7c by the LiAc method, and the selected transformant was subsequently transformed with the cDNA library plasmids. The final transformants were selected on SD plates lacking leucine/tryptophane/histidine in the presence of 20 mM aminotriazole to eliminate any false positives. Plasmids were isolated from the positive clones and back transformed into E. coli strain HB101 to amplify the plasmid DNA.

Isolation of the Full-Size PP2AC-JD cDNAs from Pea

A full-size PP2AC-JD cDNA fragment was directly identified through a yeast two-hybrid screen using a pea cDNA library constructed from dark-grown seedlings. Based on the nucleotide sequence of the PP2AC-JD cDNA clone, a 5' primer was designed as 5'-CGC GAA TTC GAT TTG GAC CAG TGG ATC-3' (SEQ ID NO: 3) and had a EcoRI restriction site (bold). The 3' primer was 5'-CGC CTC GAG TAA GAA ATA CGG AAC ACC TC-3' (SEQ ID NO: 4) and had a XhoI site (bold). The PP2AC-JD gene sequence was reamplified by the PfuTurbo polymerase that has a proof-reading activity (Stratagene) and cloned into the pGEX-4T-1 E. coli expression vector (Amersham-Pharmacia, Buckinghamshire, UK) for expression in E. coli.

DNA Sequencing and Sequence Analysis

All cDNA and DNA fragments and the junctions of the expression vector constructs were confirmed by direct DNA sequencing on both strands. DNA sequencing was carried out using the ABI PRISM 310 Genetic Analyzer (Perkin Elmer, Foster City, USA) as described in the manufacturer's manual. For each sequencing run, about 500 ng of plasmid DNA and 2–4 picomoles of 15–17 mer sequencing primer were used. Computer-assisted sequence analysis was performed using the BLAST program (NCBI, USA).

RNA Isolation

Total RNA samples were isolated from appropriate plant materials using the Rneasy Plant Total RNA Isolation Kit (Qiagen) according to the procedure supplied by the manufacturer. For quantitative RT-PCR analysis, the total RNA samples were further treated with RNAse-free DNAse I to remove any contaminating genomic DNA.

Expression and Purification of the Recombinant PP2AC-JD Protein in E. coli

The PCR product containing the PP2AC-JD gene was double-digested with EcoRI and XhoI and incorporated into the pGEX-4T-1 E. coli expression vector, resulting in pG-PP2AC-JD. In this expression construct, the PP2AC-JD gene sequence was in frame fused to the glutathione S-transferase (GST) coding sequence at the N-terminus. The vector construct was transformed into E. coli strain BL21, and the transformants were selected with 100 μg/ml ampicillin. RB medium, rather than LB, was used for induction. Two hundred fifty ml of RB (0.5% yeast extract, 1% tryptone, 0.5% NaCl, 0.2% glucose, pH 7.5 with NaOH) supplemented with ampicillin (100 μg/ml) was inoculated with 3 ml of freshly grown cell culture and incubated at 20° C. with shaking at 250 rpm to an $OD_{600}$ of 0.6. Expression was induced by adding IPTG (1 μM) and by further shaking at 20° C. for 5 hours. After centrifugation at 5000×g for 5 minutes, the cell pellet was washed in ice-cold 1×Phosphate-Buffered Saline (PBS, 140 mM NaCl, 2.7 mM KCI, 10 mM $Na_2HPO_4$, 1.8 mM $KH_2PO_4$, pH7.3). The cells were then resuspended in 5 ml of 1×PBS and lysed by repeated sonications on ice (with output of 4–5, 30 seconds×4 times). The homogenate was clarified by ultracentrifugation at 100,000×g for 30 minutes. The crude extract was concentrated 5 times using Amicon microfilter (Centriprep YM 30, Milipore) by centrifugation at 3000×g for 2–4 hours. The GST-TCTP fusion protein was purified using a Glutathione Sepharose 4B affinity column as described by the manufacturer (Promega). The purified fusion protein was then subject to thrombin digestion to remove the GST tag. Ten μl of thrombin solution (1 cleavage unit/μl ) per mg fusion protein was added, and the mixture was incubated at 0–37° C. for 15 hours. The PP2AC-JD protein was finally separated from the GST tag by a second run of the Glutathione Sepharose 4B affinity column.

Gel Electrophoresis of DNA

Agarose gel electrophoresis of DNA was usually performed using gels with a concentration range of 0.8–1.5%, depending on the size of the DNA fragments to be analyzed, using the TAE buffer (40 mM Tris-acetate, 1 mM EDTA, pH8.0). Electrophoresis was performed at a constant voltage rage of 50–200, depending on the amount of DNA loaded onto wells, for a desired time or until DNA fragments were well separated. The gel was stained with 0.5 μg/ml ethidium bromide solution, visualized on an UV transilluminator, and photographed if required.

Construction of Plant Expression Vectors

The PP2AC-JD gene sequence was reamplified using the 5' and 3' primer pair similar to those used for the $E, coli$ expression vector but with EcoRI and SadI sites and double-digested. The pBI121 (Clonetech, Palo Alto, USA) was also double-digested in an identical way. The DNA fragments were ligated using T4 DNA ligase (NEB), resulting in the pBI-PP2A-S or pBI-PP2A-AS (sense and anti-sense orientations, respectively).

Results

Isolation of a Phyto chrome A Interacting Protein Phosphatase 2A Gene

It is well established that the phytochrome photoreceptors exert a regulatory role in the photoperiodic control of flowering. In addition, recent observations suggest that the blue light absorbing cryptochromes also participate in this process and are phosphorylated by the phytochrome kinases. Several phytochrome interacting factors have been isolated through yeast two-hybrid screens, such as the PIF3, NDPK2, and PKS1.However, none of them has been confirmed to play a direct role in flowering. In addition, assuming that the reversible phosphorylation of proteins regulate a variety of cellular processes in animals and plants, a protein phosphatase, that specifically interacts with the phytochrome photoreceptors, is implicated in the regulation of flowering time and related processes. As an effort to isolate such a phytochrome interacting factor involved in flowering control, we carried out a yeast two-hybrid screen using the C-terminal domain (residues 667–1122) of the Arabidopsis phytochrome A as bait and a pea cDNA library.

One of the major positive colony groups from the yeast two-hybrid screen was a group of cDNA clones, with identical nucleotide sequences but with different lengths, that encoded the catalytic subunit of a protein phosphatase. Sequence analysis revealed that the largest cDNA clone had an uninterrupted open reading frame (ORF) (FIG. 1). The ORF consisted of 912 nucleotides, including the stop codon (TAA), that encoded a polypeptide of 303 residues. Blast searches revealed that the polypeptide was the catalytic subunit of a variant protein phosphatase (designated PP2AC-JD in the present invention) with the structural motifs characteristic of the catalytic subunits of the PP2A family (FIG. 2). The predicted PP2AC-JD protein exhibited amino acid homology of 40–45% to other members in the PP2A family. However it is evident that the PP2AC-JD is distinct from the PP2A and PPX subfamilies and can be classified as a distinct subfamily (FIG. 3). Interestingly, the PP2AC-JD has 98% sequence homology to two Arabidopsis protein phosphatases (ATPP2A1 and ATPP2A3) (FIG. 2), which strongly suggests that the two PP2As are PP2AC-JD homologues in Arabidopsis plant.

The Predominant Expression of the PP2AC-JD Gene in Flower Organ

Phytochrome A is expressed to a high level in the dark but repressed by light illumination. It was therefore anticipated that the PP2AC-JD gene would be expressed in a light-dependent manner. To get insights into the role of the PP2AC-JD, the expression pattern was accessed by RT-PCR runs using total RNAs isolated from whole plants grown for 6 days under various light conditions, including red, far-red, and far-red after red pulse lights. Unexpectedly the PP2AC-JD expression did not exhibit any light-dependence. It was expressed to an equal level under all light conditions tested (FIG. 4A), implying that its expression itself is not under the control of the phytochrome A-mediated light signals.

To examine any organ-specific expression, light-grown pea plants were dissected into leaves, stems, and roots, and total RNAs were isolated separately from each plant part. It was predominantly expressed in the flower and stalk organs, but the expression level was very low in the roots and leaves (FIG. 4B). This organ-specific expression suggests that the PP2AC-JD may have a role in the control of flowering time and/or flower architecture.

Phytochrome A as a Substrate for the PP2AC-JD

The PP2AC-JD gene was originally isolated as a phytochrome A interacting protein through yeast two-hybrid screen. Amino acid sequence analysis revealed that the encoded polypeptide is a protein phosphatase that has structural motifs conserved among the protein phosphatase 2A proteins. It was therefore predicted that the PP2AC-JD would dephosphorylate the phytochrome A photoreceptor that is autophosphorylated at residues Ser-7, Ser-17, and Ser-598 in vivo and in vitro. The recombinant PP2AC-JD protein was overexpressed as a GST fusion in $E.$ $coli$ recombinant system and purified by affinity chromatography. The recombinant PP2AC-JD was not efficiently expressed in $E.$ $coli$ cells, possibly due to a cytotoxic effect, but 0.5–1 mg could be routinely obtained in a pure form from one liter $E.$ $coli$ culture, which was enough for enzymatic and biochemical assays. A purified oat phytochrome A was autophosphorylated in the presence of γ[32P]ATP and used as a substrate for the dephosphorylation assays. A series of cations that are known to be required for the protein phosphatase activities were also examined. The phosphorylated oat phytochrome A was efficiently dephosphorylated by the PP2AC-JD only in the presence of $Fe^{2+}$ or $Zn^{2+}$, a characteristic of the PP2A family (FIG. 5A). Other cations did not show any significant stimulatory effects on the PP2AC-JD activity.

We then examined if the Pr and the Pfr phytochromes A showed differential responses to the PP2AC-JD. The purified phytochrome A was autophosphorylated under different light conditions and subject to dephosphorylation assays. The Pfr phytochrome A was more efficiently dephosphorylated by the PP2AC-JD than the Pr spectral form (FIG. 5B), suggesting that the PP2AC-JD has a more important role in the Pfr signaling. This is consistent with the fact that the Pfr form is an active form in most photomorphogenic processes.

Transgenic Arabidopsis Plants with Overexpressed or Reduced PP2AC-JD

The PP2AC-JD gene was predominantly expressed in the flower and stalk organs. The encoded PP2AC-JD dephosphorylated preferentially the Pfr phytochrome A. These observations suggested that the PP2AC-JD has a regulatory role in the phytochrome A-mediated light signal transduction for the photoperiodic control of flowering.

To investigate the role of the PP2AC-JD in flowering control, the PP2AC-JD gene was transformed into Arabidopsis plant in both the sense and anti-sense orientations, and their light responsiveness and phenotypic changes were analyzed. Arabidopsis mutant plants, that are deficient in phytochrome A, phytochrome B, and in both phytochromes A and B, were also analysed in parallel to the transgenic plants. The transgenic plants did not show any phenotypic alterations in their seedling stages in both the dark and light conditions. However they exhibited significant phenotypic changes as the plants reached the flowering stage (FIG. 6). The sense transgenic plant showed delayed flowering, which is similar to the phytochrome A null mutant. On the contrary, the anti-sense transgenic plants exhibited early flowering like the phytochrome B null mutant in a similar time course (FIG. 6). These observations indicate that the PP2AC-JD protein phosphatase is involved in the photoperiodic control of flowering in responses to light signals mediated by the phytochrome photoreceptors. This is also consistent with the organ-specific expression of the PP2AC-JD gene.

All together our data strongly support that the PP2AC-JD protein phosphatase plays a regulatory role in the photoperiodic control of flowering in response to light signals mediated by the phytochrome photoreceptors. This is the first example for the phytochrome kinase-phosphatase coupling identified with a role in a specific photomorphogenic response, the photoperiodic control of flowering. This trait is a potent agronomical target that can be applied to flowering plants to accelerate or delay the flowering time and to crop plants to redistribute the metabolic nutrients more preferentially to the vegetative organs, such as roots, stems, and leaves, rather than to the reproductive organs by delaying the flowering time, resulting in improved yields.

REFERENCES

Ahmad, M., Jarillo, J. A., Smirnova, O., and Cashmore, A. R. (1998). The CRY1 blue light photoreceptor of Arabidopsis interacts with phytochrome A in vitro. *Mol. Cell* 1, 939–948.

Blázquez, M. A. (2000). Flower development pathways. *J. Cell Sci.* 113, 3547–3548.

Devlin, P. F., and Kay, S. A. (2000). Cryptochromes are required for phytochrome signaling to the circadian clock but not for rhythmicity. *Plant Cell* 12, 2499–2509.

Guo, H., Mockler, T., Duong, H., and Lin, C. (2001). SUB1, an Arabidopsis $Ca^{2+}$-binding protein involved in cryptochrome and phytochrome coaction. *Science* 291, 487–490.

Izawa, T., Oikawa, T., Tokutomi, S., Okuno, K., and Shimamoto, K. (2000). Phytochromes confer the photoperiodic control of flowering in rice (a short-day plant). *Plant J.* 22, 391–399.

Más, P., Devlin, P. F., Panda, S., and Kay, S. A. (2000). Functional interaction of phytochrome B and cryptochrome 2. *Nature* 408, 207–211.

Mockler, T. C., Guo, H., Yang, H., Duong, H., and Lin, C. (1999). Antagonistic actions of Arabidopsis cryptochromes and phytochrome B in the regulation of floral induction. *Development* 126, 2073–2082.

Palczewski, K., Hargrave, P. A., McDowell, H., and Ingebritsen, T. S. (1982). The catalytic subunit of phosphatase dephosphorylates phosphorhodopsin. *Biochemistry* 28, 415–419.

Reed, J. W., Nagpal, P., Bastow, R. M., Solomon, K. S., Dowson-Day, M. J., Elumalai, R. P., and Millar, A. J. (2000). Independent action of ELF3 and phyB to control hypocotyl elongation and flowering time. *Plant Physiol.* 122, 1149–1160.

Stone, J. M., Collinge, M. A., Smith, R. D., Horn, M. A., and Walker, J. C. (1995). Interaction of a protein phosphatase with an Arabidopsis serine-threonine receptor kinase. *Science* 266, 793–797.

Virshup, D. M. (2000). Protein phosphatase 2A: a panoply of enzymes. *Curr. Opin. Cell Biol.* 12, 180–185.

Weigel, D., Alvarez, J., Smyth, D. R., Yanofsky, M. F., and Meyerowitz, E. M. (1992). LEAFY controls floral meristem identity in Arabidopsis. *Cell* 69, 843–859.

What is claimed is:

1. An isolated nucleic acid molecule encoding a protein or a fragment of said protein having the protein phosphatase activity that catalyzes the dephosphorylation of the phytochromes wherein said isolated nucleic acid is selected from the group consisting of:
   (a) nucleic acid molecules encoding a polypeptide having the amino acid sequence of SEQ ID NO:2; and
   (b) nucleic acid molecules comprising the coding region having the nucleotide sequence of in SEQ ID NO:1.

2. The isolated nucleic acid molecules according to claim 1, wherein the nucleic acid molecule is DNA or RNA.

3. A transformed plant cell which is stably transformed with a vector, wherein a vector contains the nucleic acid molecule having the nucleotide sequence of SEQ ID NO:1 by being ligated to one or more regulatory elements selected from promoters, terminators, and signals for polyadenylation.

4. The transformed plant cell according to claim 3, wherein the host cell is a higher plant cell.

5. A transgenic plant cell, comprising a nucleic acid molecule in antisense orientation with respect to a promoter, said nucleic acid molecule selected from the group consisting of:
   (a) nucleic acid molecule encoding a polypeptide having the amino acid sequence of SEQ ID NO:2; and
   (b) nucleic acid molecule comprising the coding region having the nucleotide sequence of SEQ ID NO:1,
   wherein the expression of the nucleic acid molecule in antisense orientation leads to a reduction of the polypeptide in plant cells.

6. A transgenic plant cell, comprising an isolated nucleic acid molecule selected from the group consisting of:
   (a) nucleic acid molecule encoding a polypeptide having the amino acid sequence of SEQ ID NO: 2; and
   (b) nucleic acid molecule comprising the coding region having the nucleotide sequence of SEQ ID NO: 1;
   wherein the expression of the nucleic acid molecule in sense orientation leads to an increase of the polypeptide in plant cells.

* * * * *